United States Patent [19]

Tiemann et al.

[11] 3,993,641

[45] Nov. 23, 1976

[54] PROCESS FOR THE PRODUCTION OF POLYISOCYANATES CONTAINING URETDIONE GROUPS

[75] Inventors: Eckhard Tiemann, Dormagen; Artur Reischl; Klaus König, both of Leverkusen; Hartmut Hetzel, Cologne, all of Germany

[73] Assignee: Bayer Aktiengesellschaft, Leverkusen, Germany

[22] Filed: Oct. 17, 1975

[21] Appl. No.: 623,284

[30] Foreign Application Priority Data
Nov. 5, 1974   Germany............................ 2452390

[52] U.S. Cl............................................. 260/239 A
[51] Int. Cl.²........................................ C07D 229/00
[58] Field of Search................................ 260/239 A

[56] References Cited
UNITED STATES PATENTS
2,683,144   7/1954   Balon et al.......................... 260/239

*Primary Examiner*—Elbert L. Roberts
*Assistant Examiner*—Dolph H. Torrence
*Attorney, Agent, or Firm*—Joseph C. Gil; Gene Harsh

[57] ABSTRACT

The instant invention is directed to a process for the continuous production of aromatic polyisocyanates containing uretdione groups. The process broadly comprising dimerizing an aromatic polyisocyanate in a continuous, coolable screw reactor at a temperature of from −30° to +70° C.

5 Claims, 1 Drawing Figure

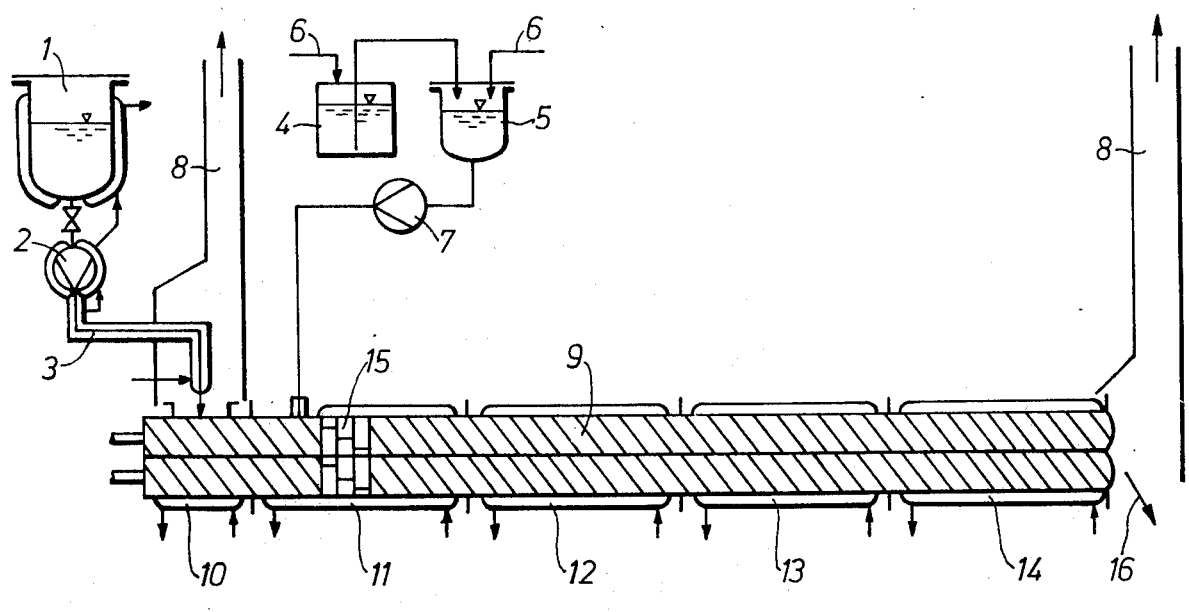

3,993,641

PROCESS FOR THE PRODUCTION OF POLYISOCYANATES CONTAINING URETDIONE GROUPS

BACKGROUND OF THE INVENTION

The production of polyfunctional uretdione isocyanates (for example, based on 2,4-tolylene diisocyanate) using dimerization catalysts, is known (Kunststoff-Handbuch, Vol. VII, Polyurethane, published by Vieweg-Hochtlen, Carl-Hanser-Verlag, Munich, 1966, page 16). In one embodiment, dimerization is carried out in an organic solvent such as dichlorobenzene (U.S. Pat. No. 2,683,144). In order to obtain high quality on a commercial scale, it has been found necessary to use higher diluted solutions. It is obvious that the use during dimerization of the large quantities of solvent which this involves and which have to be removed on completion of the reaction, involves very considerable outlay.

In another embodiment, dimerization is carried out in aqueous medium. According to U.S. Pat. No. 3,489,744, dispersants such as alkyl aryl sulphonic acids or the alkali metal salts of higher organic acids, are used. The disadvantage of this process is that a considerable proportion of the diisocyanates react with water to form ureas and polyureas, so that the products consist of a mixture of diisocyanates containing uretdione and urea groups. Additionally, dispersions prepared in this way can only be stored for limited periods because of the gradual reaction of the free NCO-groups with the water. Additional problems are involved in isolating the product from the dispersion by filtration and drying since the product is of a fine-grained nature.

To date, there has been no report of dimerization without solvents on a commercial scale. Although it is relatively easy to dimerize small quantities of aromatic diisocyanates without dilution [see, e.g., Russian Chemical Reviews, 41 (9), 1972, page 776; U.S. Pat. No. 2,671,082 and German Auslegeschrift 1,081,895], dimerization in large quantities has generally failed because of the considerable heat of reaction which has to be dissipated and also because of the liquid/liquid-solid/solid phase conversion by which the reaction is accompanied. Thus, for example, 11 kcal/mol are liberated per mol of uretdione diisocyanate produced from 2,4-diisocyanato toluene. The intense heating of the reaction mixture to temperatures of 100° C and higher results in the substantially quantitative formation of resin-like trimerization products. The trimerization products can no longer be split back into the dimers or monomers.

At one time, it appeared promising to allow the dimerization reaction to take place in thin layers on a conveyor belt (e.g., a steel belt) with cooling. However, tests have shown that the product obtained does not even begin to approach the quality of a uretdione diisocyanate prepared in dilute solution. The product still contains considerable quantities of unreacted monomeric diisocyanate, so that it smells strongly of monomeric diisocyanate. The thus-prepared uretdione isocyanate is also not uniform in its composition, because when the reaction mixture is applied to the conveyor belt even slight differences in layer thickness result in differential heating of the reaction mixture, so that relatively high quantities of isocyanurate (i.e., trimer) are formed. The reaction product can only be removed from the conveyor belt after a prolonged period, and even then only in fragments. As a result, interruptions in the continuous application of monomer are inevitable.

BRIEF DESCRIPTION OF THE DRAWING

The drawing shows a typical apparatus suitable for the process of the invention. In this drawing the numerals have following meaning:
1. Container for polyisocyanate starting material;
2. pump for polyisocyanate starting material;
3. pipe for polyisocyanate starting material;
4. storage vessel for catalyst;
5. measuring apparatus for catalyst;
6. inert gas inlet;
7. pump for catalyst;
8. vaste air outlet;
9. self-cleaning two-shaft screw reactor rotating in the same direction, closely intermeshing;
10–14. coolable resp. heatable reaction zones;
15. mixing zone;
16. outlet for reaction product.

DESCRIPTION OF THE INVENTION

It has now surprisingly been found that aromatic polyfunctional uretdione isocyanates can be continuously produced without solvents on a commercial scale in large quantities by using a continuous, coolable reactor into which the polyisocyanate free from uretdione groups used as starting substance and the dimerization catalyst are continuously introduced and mixed. It is preferred to use continuous self-cleaning reactors in order to prevent the uretdione polyisocyanate formed from settling on the walls of the reactor and hence blocking the rotating parts of the machine. It is particularly favorable to subject the solid reaction product formed to continuous, intensive mixing.

Accordingly, the present invention relates to a process for the continuous production of aromatic polyisocyanates containing uretdione groups by dimerizing aromatic polyisocyanates free from uretdione groups in the presence of catalysts which accelerate the dimerization of isocyanates at temperatures in the range of from −30° to +70° C, characterized in that dimerization is carried out in a continuous, coolable screw reactor into which the polyisocyanate free from uretdione groups to be dimerized and the dimerization catalyst are continuously introduced.

Self-cleaning screw reactors suitable for the process according to the invention are known and are described, for example, in "Schneckenmaschinen in der Verfahrenstechnik" by H. Herrmann, Springer-Verlag, Berlin/Heidelberg/New York, 1972, pages 161 to 170.

The process according to the invention may be carried out with particular advantage, in multipleshaft, preferably two-shaft screw machines with intermeshing and (except for some slight clearance) scraping pairs of screwshafts rotating in the same direction such as those described in German Pat. No. 862,668, the disclosure of which is herein incorporated by reference, or as illustrated by the drawing.

One advantage of screw machines is their continuous self-cleaning effect and forced delivery over a narrow (and even controllable) residence-time range. In addition, the screw system provides for intensive forced convection which, in addition to intensive mixing, also establishes excellent heat-transfer conditions along the inner wall of the housing, a factor which is of considerable importance to the control of the reaction temperature. Finally, the fact that the screws rotate in the same direction allows for the safe delivery and processing of products of different consistency ranging from viscous and pasty to solid, without any danger of blocking despite the intermeshing arrangement. The above-mentioned reaction passes through these various consistencies inside the screw machine, under the defined reaction conditions without any danger of crust formation. This is particularly important for the transition from pasty to solid consistency.

Surprisingly, the screw system, as used for the reaction in question, has an unexpectedly favorable coarse size-reducing effect of the solid product at the end of the screw, so that the reaction product is discharged in the form of a powdery to granular, free-flowing bulk material. So far as uretdione formation is concerned, the aforementioned screw system has proven to be not only a suitable reactor with accurately adjustable, defined and reproducible reaction conditions with very short reaction times and substantially quantitative yields, but it has also proved to be a particularly reliable apparatus for the difficult phase conversion with an unexpected size-reducing effect obtainable in the same operation.

In addition to the delivery elements with the above-mentioned, screw kinematics described in German Pat. No. 862,668 shortly after addition of the catalyst to the isocyanate stream, it is also possible to use mixing elements as described in U.S. Pat. Nos. 2,670,188 and 2,814,472, which have an increased mixing effect and intensified forced convection and, hence, provide for uniform distribution of the small quantities of catalyst in the main stream. Elements of this type may be used with advantage to enhance the mixing effect, and even enhance such effort in the reaction zone following the addition of the catalyst up to the highly viscous paste (but not in the solids zone).

The above-mentioned screw system can have one or more flights, although it is preferred to use two-flight machines with a ratio of thread depth to internal diameter of the housing of from 0.1 to 0.3, and three-flight machines with a corresponding ratio of from 0.05 to 0.15.

Although it is known to carry out organic chemical reactions in reaction screws, the reaction screws in question have generally been used for the production and modification of polymer melts at temperatures above the softening points of the particular products. The reaction products are only converted into the solid, aggregate form after discharge from the screw.

However, the reaction on which the process according to the invention is based preferably starts in a low-viscosity liquid phase. Thereafter, the reaction pass through various paste-like phases in which solid uretdione isocyanate is suspended in liquid monomers still present. In these phases, the reaction product shows a particularly marked tendency to stick and form lumps. A hard crystalline product is ultimately obtained after reaction of the monomer. It has not been expected that chemical reactions passing through such contrary aggregate states would be able to be carried out in screw machines of the type described. It is particularly surprising that it is possible for the first time, using screw machines to keep the known dimerization reaction of aromatic polyisocyanates, carried out on a commercial scale in the substantial absence of solvents, under such effective control that substantially pure dimerization products, i.e. dimerization products free from isocyanurate groups, are obtained. It is particularly surprising that a fine, free-flowing powder which may be used without further grinding for numerous applications, is actually discharged from the screw.

Aromatic polyisocyanates preferably used for the process according to the invention include diisocyanates corresponding to the following general formula:

$$R(NCO)_2$$

wherein R represents an aromatic hydrocarbon radical having a total of from 6 to 15 carbon atoms, optionally substituted by alkyl, alkoxy, phenoxy or halogen radicals and/or optionally containing alkylene radicals between two aromatic rings as bridge members.

Examples of aromatic isocyanates of this type include: 2,4-diisocyanato toluene, 2,6-diisocyanato toluene, and mixtures of these isomers; 4,4'-diisocyanato diphenyl methane; 4,4'-diisocyanato diphenyl propane; 1,4-diisocyanato2-chlorobenzene; 4,4'-diisocyanato-3,3'-dichlorodiphenyl methane; 1,4-diisocyanato-3-methoxy benzene; and 1,4-diisocyanato-3-phenoxy benzene. Diisocyanates preferably used for the process according to the invention are 2,4'-diisocyanato toluene, 2,6-diisocyanato toluene, and mixtures of these isomers; or 4,4'-diisocyanato diphenyl methane. It is particularly preferred to use 2,4-diisocyanato toluene. In particular cases, it is also possible to use, preferably as mixture components, tri- and higher functional aromatic polyisocyanates or even modified polyisocyanates containing urethane or urea groups, for example, the addition product of 5 mols of 4,4'-diphenyl methane diisocyanate and 1 mol of tripropylene glycol. In cases where high-melting diisocyanates are used, it can be of advantage to add small quantities of organic solvents in order to lower the melting point.

Catalysts suitable for use in the process according to the invention are known and include any substances which accelerate the dimerization of aromatic polyisocyanates to form uretdione groups. It is preferred to use tertiary aliphatic or heterocyclic amines, such as triethyl amine, tri-n-propyl amine, N-methyl and N-ethyl morpholine and pyridine. However, it is particularly preferred to use phosphines corresponding to the following general formula:

$$R_1-\underset{\underset{R_3}{|}}{\overset{\overset{R_2}{|}}{P}}$$

wherein
R$_1$ represents an aliphatic hydrocarbon radical having from 1 to 18 carbon atoms; and
R$_2$ and R$_3$ which may be the same or different, each represent an aliphatic hydrocarbon radical having from 1 to 18 carbon atoms, or a phenyl radical.

In the process according to the invention, the catalysts are used in such quantities that the dimerization reaction takes place substantially quantitatively over a period of up to 60 minutes, preferably from 1 to 3 minutes, at the reaction temperature selected which is defined in more detail hereinafter. The catalysts are generally used in quantities of from 0.001 to 2% by weight, and preferably in quantities of from 0.05 to 0.5% by weight, based on the weight of the starting diisocyanate to be dimerized. In order accurately to dose relatively small quantities of catalyst, it is of advantage to dissolve the catalyst in an organic, solvent. However, the quantity in which the solvent is used should not exceed 20% by weight, preferably 5% by weight, based on the starting isocyanate.

The process according to the invention is preferably carried out in the absence of solvents. However, the above-mentioned small quantity of solvent optionally used for dissolving the catalyst is harmless. These small quantities of solvent may readily be removed by evaporation during or after the reaction in the screw machine. In the case of extremely large throughputs, and with particularly intensive cooling, it is of course also possible to use larger quantities of catalyst. Naturally, the catalyst will be used in the smallest possible quantities necessary to obtain a product of high purity.

It is essential in the process according to the invention to maintain a temperature in the range of from −30° to +70° C. As is known, this can readily be achieved by equipping the reactor with several independently controllable temperature zones. Naturally, the reactor must be cooled most intensively where the greatest amount of heat is liberated. On the other hand, the temperature should not be too low because otherwise the reaction velocity becomes too low. The reactor may even be heated at its inlet in cases where solid starting material is to be melted before the reaction.

The temperature of the reaction product should not exceed 70° C during uretdione formation and before destruction of the catalyst. Reaction temperatures in the range of from −20° to 40° C are preferred, reaction temperatures in the range of from 0° to 20° C being particularly preferred.

One particular advantage of the process, is that through crystallization and precipitation, the uretdione isocyanates which are generally insoluble in the monomer are prevented from the further reaction to form the trimer and from splitting back into the monomer so that the reaction is substantially quantitative with hardly any free diisocyanate left in the end product. In general, the catalyst may be destroyed on completion of the reaction by the addition, optionally at the end of the screw machine, of catalyst poisons, such as alkylating agents, acids, elemental sulphur, atmospheric oxygen or pure oxygen. Since the catalysts are generally only used in very small quantities, they need not be destroyed for certain applications, especially in cases where the starting diisocyanate contain isocyanate groups differing distinctly in their reactivity, as in the case of for example, 2,4-diisocyanato toluene.

The starting polyisocyanate is preferably introduced into the screw machine by known means such as a metering pump either through a hopper opening in the machine equipped with a suction system and, optionally, with a nitrogen inlet, or preferably through a tube into the otherwise uninterrupted screw inlet housing. In both cases, complete or partial filling of the screw thread zone in the feed zone can be obtained by varying the rotational speed of the screw. The catalyst can be introduced by means of a second metering pump, preferably at a second point situated slightly downstream in the screw machine, and is only combined with the polyisocyanate inside the screw machine, the two components being intensively intermixed and continuously scraped off the mixing tool and reactor wall.

In order to obtain economic operation of the multiple-shaft screw machine, it is also possible to carry out the initial phase of the reaction, i.e. until the uretdione isocyanate begins to crystallize, in this screw machine and then to complete the reaction in a following screw machine, for example, in a single shaft screw machine or in a continuous mixer.

The end products obtained by the process according to the invention, more especially in uredione diisocyanate based on 2,4- and/or 2,6-diisocyanato toluene, may be used as blocked diisocyanates for the production of lacquers, for bonding tire cord and for corsslinking polyurethane elastomers. In addition, fine powders of these products may be suspended in water by means of emulsifiers and used as adhesives from the aqueous phase.

The end products obtained by the process according to the invention may if desired be modified by additions of plasticizers, dyes, emulsifiers (in order to disperse the end products in water), inorganic or organic fillers, levelling agents, stabilizers, or antioxidants. These additives may be added, for example, at the beginning or end of the screw.

The invention is further illustrated, but is not intended to be limited by the following examples in which all parts and percentages are by weight unless otherwise specified.

EXAMPLE 1

1,3% of tributyl phosphine (percent, by weight based on tolylene diisocyanate) are continuously added to 2,4-tolylene diisocyanate at a temperature of 10° C in a two-shaft screw machine with intermeshing screw-shafts rotating in the same direction.

The housing of the 1845 mm long screw shafts is divided up into four cooling zones of equal length. The cooling media in these cooling zones have the following temperatures:

| | | |
|---|---|---|
| 1st zone | −10° C | (cooling medium: brine) |
| 2nd zone | −20° C | (cooling medium: methanol) |
| 3rd zone | −20° C | (cooling medium: methanol) |
| 4th zone | 0° C | (cooling medium: brine) |

The product issuing from the screw has a temperature of 15° C.

| | |
|---|---|
| Throughput: | 40 kg/h |
| Residence time: | 1.7 mins |
| Screw speed: | 80 rpm |
| External diameter of screw shafts: | 53 mm |
| Internal diameter of screw shafts: | 42 mm |
| Length of screw shafts: | 1845 mm |

Analyses:
NCO-content (titrimetric):
found: 24.5 %;
calculated: 24.15 %.
NCO-content (titrimetric) of the split-back uretdione diisocyanate.
found: 47.1 %;
calculated: 48.3 %.
Results of gel chromatographic analysis (% by weight):

| Residual Quantity of monomers | Uretdione isocyanate | Polyuretdione isocyanate and trimerization products |
|---|---|---|
| < 0.8 | 96 | 3 |

Average grain size: 150 μ

In a variant of the Example, the catalyst used was destroyed by adding 120% of the equivalent quantity of sulphur 20 cm before the product outlet, in order thus to obtain a corresponding, but almost indefinitely storable product.

EXAMPLE 2

The procedure is as in Example 1 using 4,4'-diphenyl methane diisocyanate.

| Cooling zone temperatures: | |
|---|---|
| 1st cooling zone: | 30° C |
| 2nd cooling zone: | −15° C |
| 3rd cooling zone: | −15° C |
| 4th cooling zone: | − 5° C |
| Temperature of the issuing product: | 15° C |

Analyses:
NCO-content (titrimetric): found: 30.8 %; calculated: 33.6 %.

EXAMPLE 3 (Comparison)

1.2 kg/min of 2,4-tolylene diisocyanate is mixed at room temperature with 1.3% by weight, of tributyl phosphine in a Kenics mixer, and distributed onto an endless belt from a traversing distributor (length of belt: 30 m, coating width: 50 cm, belt speed: 75 cm/min). For cooling, air at 12° C is blown onto the underside of the belt. The belt is thus maintained at a constant temperature of 15° C. In spite of this, the temperature at the surface of the product rises to 48° C. When the product reaches the rear reversing drum of the belt; the belt has to be stopped to enable the reaction product to harden. This after-reaction is necessary to prevent the reaction product from separating from the belt.

Part of the film of product was removed from the belt and a sample ground-up. Analysis gave the following values (% by weight):

| Residual quantity of monomer | Uretdione diisocyanate | Polyuretdione diisocyanates and trimerization products |
|---|---|---|
| 7 | 70.2 | 22.8 |

Another part of the film of product was split into two layers. The analyses of the two layers are shown in the following Table:

Analyses: (gel chromatography, % by weight)

| | Residue of monomer | Uretdione isocyanate | Polyuretdione diisocyanates and trimerization products |
|---|---|---|---|
| upper half of layer | 8 | 65.1 | 25.1 |
| lower half of layer | 5 | 80.5 | 15.0 |

EXAMPLE 4 (Comparison)

1.58 g of tributylphosphine (1.0% by weight, of tributyl phosphine, based on tolylene diisocyanate) are added with vigorous stirring at 20° C to 150 g of 2,4-tolylene diisocyanate contained in a glass beaker. The liquid mixture solidifies after about 1 minute (temperature 75° C). The solid product becomes liquid again for 5 minutes (temperature 103° C). After a few hours, it hardens to form a glass-like product.

What is claimed is:

1. A process for the continuous production of aromatic polyisocyanates containing uretdione groups comprising: dimerizing aromatic polyisocyanates free from uretdione groups in the presence of catalysts which accelerate the dimerization of isocyanates at temperatures in the range of from −30° to +70° C, wherein dimerization is carried out in a continuous, coolable screw reactor into which the polyisocyanates free from uretdione groups to be dimerized and the dimerization catalyst are continuously introduced.

2. The process of claim 1, wherein the reaction is carried out in a multiple-shaft screw machine.

3. The process of claim 2 wherein the reaction is carried out in a two-shaft screw machine with intermeshing screw shafts rotating in the same direction.

4. The process of claim 1, wherein 2,4-diisocyanato toluene is used as the aromatic polyisocyanate free from uretdione groups.

5. The process of claim 4, wherein the dimerization catalyst used is a phosphine corresponding to the following general formula:

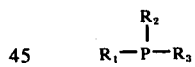

wherein
   $R_1$ represents an aliphatic hydrocarbon radical having from 1 to 18 carbon atoms; and
   $R_2$ and $R_3$ which may be the same or different each represent an aliphatic hydrocarbon radical having from 1 to 18 carbon atoms or a phenyl radical.

* * * * *